US005304367A

United States Patent [19]

Biegon

[11] Patent Number: 5,304,367
[45] Date of Patent: Apr. 19, 1994

[54] IN VIVO BRAIN IMAGING AGENT AND METHOD FOR DIAGNOSIS OF PSYCHIATRIC DISORDERS

[75] Inventor: Anat Biegon, New York, N.Y.

[73] Assignee: New York University, New York, N.Y.

[21] Appl. No.: 614,434

[22] Filed: Nov. 16, 1990

[51] Int. Cl.$^5$ .............................................. A61K 49/02
[52] U.S. Cl. ................................................... 424/1.11
[58] Field of Search ........................................ 424/1.1

[56] References Cited

U.S. PATENT DOCUMENTS 4,311,685 1/1982 Snyder ................................ 424/1.1
4,970,238 11/1990 Louis et al. ......................... 514/652

OTHER PUBLICATIONS

Weinberger, D. R. et al., *Adv. Neurol.* 51:147-150 (1990).
Antoni, G. et al., *Appl. Radiat. Isot.* 40:561-564 (1989) (*Int. J. Radiat. Appl. Instrum. Part A*).
Wagner, H. N., Jr., In: *Quantitative Receptor Autoradiography*, Boast, C. A. et al., eds., Alan R. Liss, Inc., 1986, pp. 233-254).
Hughes, B. et al., *Nuc. Med. Biol.* 13:565-71 (1986).
Hughes, B. et al., *J. Nucl. Med.* 27:66-667 (1986).
Tondo, L. et al., *J. Pharmacol. Exp. Ther.* 235:1-1 (1985).
Conway, P. G. et al. *J. Pharmacol. Exp. Ther.* 241:755-62 (1987).
Rainbow, T. C. et al., *J. Neurosci. Meth.* 5:127-138 (1982).
Rainbow, T. C. et al. *Proc. Natl. Acad. Sci. USA* 81:1585-89 (1984).
Kuhar, M. J. In: *Quantitative Receptor Autoradiography*, Boast, C. A. et al., eds., Alan R. Liss, Inc., 1986, pp. 1-12.
Mann, J. J. et al., *Arch. Gen. Psychiat.* 43:954-959 (1986).
Biegon, A. et al., *Brain Res.* 442:199-203 (1988).
Garvey, H. L. et al. *J. Pharmacol. Exp. Ther.* 194:220-233 (1975).
Arendt, R. M. et al. *Cardiology* 71:307-314 (1984).
Arnett, C. D. et al. *J. Neurochem.* 44:835 (1985).
Arnett, C. D. et al., *J. Nucl. Med.* 27:1878 (1986).
Kinsey, B. et al. Abstract for Soc. Nucl. Medicine 38th Ann. Meeting, Jun. 11-14, (1991).
Tewson, T. J. et al. (abstract 7) and Kinsey, B. M. et al., abstract (source known).
Tewson, T. J. et al., Paper from 1986 Radio-pharmaceutical Chemistry Meeting, Boston, pp. 388-90.
Moretti-Rojas et al, "Serotonergic and Adrenergic Regulation . . . ," *J. Biol. Chem*, vol. 258, No. 20, Oct. 25, 1983, pp. 12499-12508.
Hughes et al, "Characterization of Beta-Adrenoreceptors . . . ", *J. Nucl Med*, vol. 27(5), 1986, pp. 660-667.

*Primary Examiner*—Robert L. Stoll
*Assistant Examiner*—John M. Covert
*Attorney, Agent, or Firm*—Browdy and Neimark

[57] ABSTRACT

A composition useful as an imaging agent comprises a beta adrenergic receptor antagonist compound, preferably iodopindolol, to which is covalently attached an iodine radioisotope such as $^{123}$I or $^{124}$I. This composition is used in a method for radioimaging beta adrenergic receptors in a tissue, preferably brain. In particular, the method is useful with the radioimaging technique of single photon emission computed tomography (SPECT) or positron emission tomography (PET). The above composition, as well as a kit comprising a set of one or more standard radiographic images of beta adrenergic receptors, are also useful in methods for (1) diagnosing an alteration in beta adrenergic receptors in a tissue, particularly brain; (2) diagnosing suicidal depression in a subject; and (3) detecting the therapeutic normalization of beta adrenergic receptor expression in a subject.

4 Claims, 4 Drawing Sheets

IN VIVO BRAIN IMAGING AGENT AND METHOD FOR DIAGNOSIS OF PSYCHIATRIC DISORDERS

BACKGROUND OF THE INVENTION

Field of the Invention

The invention in the area of neurobiology and nuclear medicine relates to imaging agents useful for imaging beta adrenergic receptors in the brain and methods of using these agents for diagnosis of depression and prognosis of suicidal depression.

Description of the Background Art

Depression is the most common psychiatric disorder, affecting up to 10% of the general population at some point in life (Charney, E. A. et al., In: *Depression and Mania*, A. Georgotas et al., Eds. Elsevier, New York, 1988, pp. 26-52). A history of depression is a serious risk factor for suicide, being present in 40 to 60% of suicide victims (Rosen, D. H., JAMA 235 (1976) 2105-2109).

Depression is commonly treated with antidepressant drugs or electroconvulsive therapy (ECT). Early studies of the effects of antidepressants on the brain led to the formulation of the catecholamine theory of depression (Schildkraut, J. J., *Am. J. Psychiat.* 122 (1965) 509-522). The catecholamine theory postulates that a deficit of the neurotransmitter norepinephrine (NE) in relevant synapses in the brain is responsible for the syndrome. This was based on the observations that different classes of drugs with antidepressant activity had the common action of increasing central NE activity, either by inhibition of NE reuptake (the tricyclic antidepressants) or by inhibition of NE metabolism (the monoamine oxidase, or MAO, inhibitors). One complication in this apparently simple relationship was the fact that, while inhibition of NE reuptake or MAO activity occurs within minutes of drug administration, the clinical response to antidepressants (and to ECT) is usually delayed, often requiring 2-3 weeks.

More recent approaches to understanding the neurochemical basis of depression have therefore focused on the chronic, rather than the acute, effects of antidepressants and ECT on various neurotransmitter systems (See, for example, Abel, M. S. et al., *Biochem. Pharmacol.* 34 (1985) 679-683; Antkiewicz-Michaluk, L. et al., *Eur. J. Pharmacol.* 102 (1984) 179-181; Banerjee, S. P. et al., *Nature* 268 (1977) 455-456; Bergstrom, D. A. et al., *J. Pharmacol. Exp. Ther.* 209 (1979) 256-261; Charney, D. S. et al., *Arch. Gen. Psychiat.* 38 (1981) 1160-1180; Kellar, K. J. et al., *J. Neurochem.* 37 (1981) 830-836; Kinnier, W. J. et al., *Eur. J. Pharmacol.* 67 (1980) 289-294;; Mobley, P. L. et al., In: *Antidepressants: Neurochemical, Behavioral and Clinical perspectives*, Enna S. J. et al., eds. Raven Press, New York, 1981, pp.31-55; Plenge, P. et al., *Psychopharmacol.* 77 (1982) 94-97; Reisine, T. et al., *Eur. J. Pharmacol.* 77 (1982) 39-44; Vetulani, J. et al.. *Naunvn- Schmied Arch. Pharmacol.* 293 (1976) 109-114).

The literature which chronicles the effects of chronic antidepressant therapy or ECT on serotonergic, noradrenergic, dopaminergic and opioid systems in the brain is somewhat confusing and contradictory (See, for example, Antkiewicz-Michaluk, L. et al., supra; Charney, D. S. et al., supra: Kinnier, W. J. et al., supra; Plenge, P. et al., supra; Reisine, T. et al., supra). However, the most consistent and best substantiated findings from these studies concern effects on beta adrenergic receptors ($\beta$AR), one of the major sites of action of NE.

Using Scatchard analysis (see below) of the binding isotherms of $\beta$AR ligands, several studies have consistently shown that chronic, but not acute, treatment of experimental animals with tricyclic antidepressant drugs leads to a reduction in the density of brain $\beta$AR (expressed as maximum binding, Bmax) with no concomitant change in receptor affinity (expressed as the dissociation constant, Kd).

The changes in receptor density are functionally significant since they are coupled to reduced receptor responsiveness, measured as NE-stimulated adenylyl cyclase activity, which is the classic post-binding biochemical event in this system (Abel, M. S. et al., supra; Banerjee, S. P. et al., supra; Bergstrom, D. A. et al., supra; Kinnier, W. J. et al.,supra; Vetulani, J. et al., supra). Repeated, but not single, administrations of ECT also caused similar drops in $\beta$AR density or responsiveness (Abel, M. S. et al., supra; Kellar, K. J. et al., supra). The same is true for MAO inhibitors and for several of the new generation of "atypical" antidepressants. These findings have led some to conclude that down regulation (i.e. decrease in receptor density and-/or fall in adenylyl cyclase activity in response to receptor stimulation) of brain $\beta$ARs is the single pathway common to the various treatment modalities which counter depression (Mobley, P. L. et al., supra: Vetulani, J. et al., supra).

Earlier studies in rats on the effects of antidepressants or ECT on $\beta$AR were performed using homogenates prepared from large brain regions, such as whole forebrain or frontal cortex. However, $\beta$AR are now known to be heterogeneously distributed in the rat brain (Rainbow, T. C. et al., *Proc. Natl. Acad. Sci. USA* 81 (1984) 1585-1589). Using autoradiography to permit localization of changes, as well as dissection and homogenization techniques to analyze receptor saturation parameters, the present inventors and their collaborators, as well as others, have shown that the down regulation of $\beta$AR caused by antidepressants and ECT is anatomically selective (Biegon, A. et al., *Eur. J. Pharmacol.* 123 (1986) 329-334; Biegon, A., *J. Neurochem.* 47 (1986) 77-80; Kellar, K. J. et al., supra; Stanford, S. C. et al., *J. Neurosci.* 7 (1982) 175-183). The regions most affected are the frontal cortex and the hippocampus.

In a limited autoradiographic study of $\beta$AR in the brains of suicide victims, the present inventors and their colleagues have found higher density of $\beta$AR in the suicides compared to pair-matched controls (Biegon, A. et al., *Brain Res.* 442 (1988) 199-203; Zanko, M. et al., *Soc. Neurosci. Abstr.* 9 (1983) 879). This difference exists in the prefrontal cortex but not in the caudate or putamen. Others have confirmed these observations (Mann, J. J. et al., *Arch. Gen. Psychiat.* 43 (1986) 954-959).

Despite the compelling evidence for the involvement of $\beta$AR in depression and its treatment, relatively little is known about the biology and biochemistry of these receptors in the human brain, such as their precise distribution throughout the brain, the localized or general influence of age, sex, and other factors on the receptors, and their actual response to antidepressant treatment. A few postmortem studies on a small number of grossly dissected, homogenized brain regions have documented the presence of $\beta$AR in the human brain (Cash, R. et al., *Brain Res.* 322 (1984) 269-275; Shimohana, S. et al., *J. Neurochem* 48 (1987) 1215-1221; Whitehouse, P. J. et al., *Soc. Neurosci. Abstr.* 14 (1988) 1223), and their possible involvement in Parkinson's disease and Alzheimer's disease. No effects of age or sex were reported, most probably because the number of brain regions and the number of women included in the analysis were too low. A preliminary autoradiographic study described the distribution of βAR subtypes in the human postmortem brain (Pazos, A. et al., *Brain Res.* 358 (1985) 324-328). An important advantage of the autoradiographic approach to brain receptors is the ability to study relationships between different neurotransmitter systems, since serotonergic, cholinergic and opioid systems may be studied in consecutive sections from the same brains (Gross-Isserof, R. et al., *J. Neurochem.* 51 (1988) 528-534; *Brain Res.* 507 (1990) 208-215; *Arch. Gen. Psychiat.* 46:237-242 (1989). In order to firmly establish a role for brain βAR in depression and suicide, it is necessary to demonstrate that these receptors undergo dynamic changes in response to depression and to antidepressant therapy. This can be accomplished only through in vivo receptor imaging.

In vivo imaging of βAR in the human brain had not been accomplished prior to the work of the present inventors. An increasing number of neurotransmitter receptors, including receptors for dopamine, opiods, benzodiazepine, serotonin and acetylcholine, have been visualized in the brains of humans or animals using either positron emission tomography (PET) or single photon emission computed tomography (SPECT) (Kung, H. F., *Nucl. Med. Biol.* 17 (1990) 85-92; Wagner, H. N., Jr., In: *Quantitative receptor autoradiography*, Boast C. A. et al., eds., Alan R. Liss Inc., New York, 1986, pp. 233-254); Shiue et al., U.S. Pat. No. 4,871,527). Several βAR ligands have been labelled with $^{11}$C and used for cardiac imaging with PET (Antoni G. et al., *Appl. Radiat. Isot.* 40 (1989) 561-564; Syrota, A., *New Concepts Cardiac Imag.* 4 (1988) 141-166); however, no studies utilizing these ligands in brain have been reported.

Widespread use of PET imaging of βAR (or any other receptor) as a diagnostic approach does not appear to be as likely as more economical imaging approaches. First, there are high costs associated with purchase and maintenance of PET equipment, making PET facilities rather scarce. Furthermore, many of the imaging agents useful in PET require cyclotrons or reactors for their production, have short half lives (e.g. 110 minutes for $^{18}$F, 20 minutes for $^{11}$C), virtually necessitating production at their site of use, and resulting in emissions of extremely limited duration.

In contrast to PET, SPECT imaging is not subject to such costs and limitations. SPECT imaging is now a routine part of nuclear medicine. Commercially available agents are being used to study cerebral blood flow in a variety of clinical conditions. Investigators using SPECT have demonstrated changes in cerebral blood flow associated with unipolar and bipolar depression (Rush, A. J. et al., *Psychopharm. Bull.* 18 (1982) 6-8). The new generation of dedicated, multi-headed SPECT cameras have greater sensitivity and resolution, facilitating the feasibility of this technique for imaging brain receptors. For example, SPECT was recently employed to probe human brain cholinergic muscarinic receptors using [$^{123}$I]iodo-QNB as the receptor ligand (Weinberger, D. R. et al. *J. Nucl. Med.* 30 (1989) 896; *Adv. Neurol.* 51 (1990) 147-150). Use of this radioligand gave the expected distribution of muscarinic M1 and M2 receptors and showed abnormalities of receptors in the brains of patients with Pick's disease and Alzheimer's disease.

Iodopindolol is a well characterized βAR antagonist with very high affinity (<1 nM) and specificity (Barovsky, K. et al., *J. Cyc. Nucl. Res.* 6 (1980) 297-307). Unlike most other βAR antagonists, iodopindolol has a low affinity for serotonin receptors of the $5HT_{1B}$ and $5HT_{1D}$ subtypes. This agent also crosses the blood brain barrier and labels both βAR subtypes, β1 and β2, in vivo in experimental animals (Conway, P. G. et al., *J. Pharmacol. Exp., Ther.* 241 (1987) 755-762; Tondo, L. et al., *J. Pharmacol. Exp. Ther.* 235 (1985) 1-9). A preparation of $^{123}$I-iodopindolol which is sterile and safe for human use is not currently available. The parent compound, pindolol, is an approved beta blocking drug used clinically to treat hypertension. while pindolol itself is safe at the dose ranges commonly taken by patients over prolonged periods, there has been no evaluation of the toxicity of the iodinated compound.

Once a with a suitable imaging approach various aspects of depression can be examined For example, depressed suicidal patients can be compared to pair-matched controls to evaluate differences in βAR distribution in vivo between the two groups. Scanning the same patients following therapeutic intervention (drugs or ECT) will provide the first direct look in humans at the behavior of brain βAR under the therapeutic influence of antidepressants, and will substantiate the regional specificity of any alterations.

SUMMARY OF THE INVENTION

An object of the present invention is to overcome the deficiencies in the work described above.

The present invention is directed to a composition useful as an imaging agent comprising a beta adrenergic receptor antagonist compound to which is covalently attached the radioisotope $^{123}$I, and an administering medium suitable for intravenous injection, the compound being present in an amount sufficient to produce a radioimage of tissue using radioimaging techniques. A preferred compound is iodopindolol.

In another aspect, the present invention is directed to a method for radioimaging beta adrenergic receptors in a tissue of an animal comprising: (a) administering intravenously the above imaging agent; (b) allowing a sufficient amount of time for the above compound to enter the tissue to be imaged and for a radioactive portion of the compound to become immobilized within the tissue; and (c) recording a radioimage of the tissue using radioimaging techniques. The method is particularly useful for imaging human brain. In particular, the method is useful employing the radioimaging technique of single photon emission computed tomography (SPECT).

The method described above is useful for diagnosing an alteration in beta adrenergic receptors in a tissue in a subject, particularly in brain by carrying out the above method and comparing to a control.

The present invention is also directed to a method for diagnosing suicidal depression in a subject comprising radioimaging the beta adrenergic receptors in the brain of the subject according to the above method and comparing to an image of beta adrenergic receptors known to be associated with suicidal depression.

The present invention is also directed to a method of detecting the therapeutic normalization of beta adrenergic receptor expression in a subject having abnormal density or distribution of these receptors comprising radioimaging the beta adrenergic receptors in a tissue, preferably brain, of the subject and comparing to a control according to the above method.

In another embodiment, the present invention is directed to a kit useful for diagnosing an alteration or normalization of beta adrenergic receptors in a tissue, preferably brain, in a subject using a radioimaging technique; this kit contains a set of one or more standard control radiographic images of the tissue having normal density and distribution of the receptors, wherein the information obtained by the radioimaging technique can be compared to the radiographic images contained in the kit to allow determination of the alteration or normalization of receptor expression.

Also provided is a kit which is useful for diagnosing suicidal depression in a subject in conjunction with a radioimaging technique which determines an increase in the number of beta adrenergic receptors in the brain; this kit includes a set of one or more standard radiographic images of enhanced beta adrenergic receptor expression in the brain known to be associated with suicidal depression, wherein the information obtained by the radioimaging technique can be compared to the radiographic images, allowing diagnosis of suicidal depression.

The standard radiographic images of the above kits can be autoradiograms, preferably in the form of a two-dimensional photograph or in the form of a three-dimensional digitized computer image adapted to the type of radioimaging being used.

BRIEF DESCRIPTION OF THE DRAWINGS

FIG. 2 is an autoradiogram showing total $^{125}$I-iodopindolol binding to a sagittal brain section from a normal male subject. The nonspecific binding of the radioligand in the presence of the beta blocker, propranolol, is low and uniform throughout the section.

FIG. 3 shows the distribution of $\beta_1$ receptors, labeled by iodopindolol in the presence of zinterol (a selective $\beta_2$ receptor antagonist), on a consecutive section from the same brain as FIG. 2.

FIG. 4 shows the distribution of $\beta_2$ receptors, labeled by iodopindolol in the presence of metoprolol (a selective $\beta_1$ receptor antagonist), on a consecutive section from the same brain as FIGS. 2 and 3.

DESCRIPTION OF THE PREFERRED EMBODIMENTS

Animal experiments with antidepressant drugs have shown that beta adrenergic receptors ($\beta$AR) in the brain respond in a consistent manner to treatment with such agents. The present inventors have studied human postmortem brains and have discovered that the concentration and distribution of these receptors is altered in the brains of suicide victims. This prompted the present inventors to conceive of the present invention which is concerned with compositions and methods useful for in vivo imaging of $\beta$AR, particularly in the brain.

In particular, the inventors have developed an imaging agent comprising iodopindolol, a $\beta$AR ligand, useful in single photon emission tomography (SPECT), and methods for its production and use. In addition to use in suicide and depression, the compositions and methods of the present invention are useful for imaging beta receptors in the brain, and in other tissues such as heart, blood vessels or lung, for example, in conjunction with the diagnosis or treatment of any disease affecting such receptors. For example, the present invention may be used for imaging of the heart or vasculature in patients with hypertension, the lungs and bronchial passages in asthma, and in other organs and diseases which are known to those of skill in the art.

The present invention is also intended to encompass similar radioimaging agents, methods, and kits useful in PET. rather than preparing $^{123}$I-iodopindolol, as described herein, $^{124}$I-iodopindolol is prepared for use in PET. The positron emitting isotope is prepared and used using methods known in the art. For general information on PET, see, for example: Phelps, M. E. et al., *Positron Emission Tomography and Autoradiography.* Raven Press, New York, 1986.

The present inventors have studied the distribution of $\beta$AR in the human brain of both controls and suicides by quantitative in vitro autoradiography (Kuhar, M. J., *Quantitative Receptor Autoradiography,* Boast C. A. et al., eds., Alan R. Liss, New York, 1986, pp.1-12; Rainbow, T. C. et al., *J. Neurosci. Methods* 5 (1982) 127-138), a technique that allows fine anatomical resolution without sacrificing the quantitative character of homogenate binding studies. The nature of the localization of $\beta$AR in the human brain, including local receptor regulation by factors such as age, sex and disease state (e.g., suicide). Since both age and sex are risk factors in depression, the effects on these variables on $\beta$AR are of value in providing a comprehensive biological explanation and establishing a data base for the study of $\beta$AR in other pathological or physiological situations.

Their observations have led the present inventors to a hypothesis stating that suicidal depression is associated with an abnormal distribution pattern of brain $\beta$AR, which can be characterized with high anatomical resolution not only by quantitative in vitro autoradiography but by radioimaging methods, in particular SPECT, in vivo. Successful treatment of depression would then normalize the receptor distribution, a change which can also be detected by SPECT using the compositions and methods of the present invention. As a result of the utilization of the compositions and methods of the present invention, SPECT scanning of brain $\beta$AR will become a tool for diagnosis and monitoring of treatment outcome in depressed and suicidal patients.

Brain Collection

Brains used for post-mortem analysis are excluded post hoc if there are signs of neuropathology or drugs in the brain discovered during the autopsy and the following toxicological tests. Brains are also excluded if there is a postmortem delay (PMD), defined as time between death and autopsy, of more than 48 hours.

At autopsy, the brains are removed from the cranium and cut into approximately 2.5 cm blocks which are frozen in powdered dry ice. Typically the left hemisphere is cut into sagittal blocks while the right hemisphere is cut in the coronal plane. After freezing, the brains are transported in dry ice and stored frozen at about $-70°$ C. until used. Prior to sectioning, the blocks are embedded in an embedding agent, such as 3.5% carboxymethyl cellulose. Other embedding agents are well-known to those of ordinary skill in the art. Coronal and sagittal sections, about 40 $\mu$m thick, are cut on a cryotome (e.g., a Bright whole body cryotome) at about $-15°$ C., thaw mounted onto gelatin coated slides and kept overnight at about $-20°$ C. prior to the autoradiographic procedure.

Beta Receptor Autoradiography

Iodopindolol is a well characterized $\beta$AR antagonist with a very high affinity ($<1$ nM) and specificity (Barovsky, K. et al., supra). Receptor binding studies are performed according to techniques well known in the art (see, for example, Kuhar, M. J., supra; Rainbow, T. C. et al., 1982, 1984, supra). A preferred method is described herein, although it will be apparent to one of skill in the art that the disclosed method may be modified according to the tissue preparation and ligand used.

Slides holding tissue sections are incubated for about 70 min at approximately 25° C. with 0.15 nM $^{125}$I-iodopindolol (New England Nuclear, 2200 Ci/mmole) in 25 mM Tris buffer, pH 7.5, containing 150 mM NaCl. Nonspecific binding is determined in the presence of 1 $\mu$M propranolol (see Examples, below). Zinterol, a selective $\beta$2 blocker, or metoprolol, a selective $\beta$1 antagonist, are added to the incubation buffer at 0.1 $\mu$M to achieve selective labeling of the $\beta$1 and $\beta$2 receptor subtypes, respectively. The incubation is followed by three 20 min washes in the same ice cold buffer. Slides are then dipped in ice cold distilled water to remove buffer salts, dried on a 50° C. slide warmer and apposed to $^3$H-sensitive film (Amersham $^3$H-hyperfilm) for 48–96 hours. The film is coexposed to commercial iodine standards (available from Amersham, for example). Film is developed manually using standard developer and fixer such as those available from the Eastman-Kodak Company. Sections are stained with cresyl violet and structures identified from the stained sections with the assistance of atlases and neuroanatomical texts such as: Barr M. L., *The Human Nervous System: An Anatomical Viewpoint*. Harper and Row, New York (1974); Carpenter M. B., *Human Neuroanatomy*. Williams and Wilkins, Baltimore (1976); DeArmond S. J. et al., *Structure of the Human Brain: A Photographic Atlas*. Oxford University Press, New York (1974); Nieuwenhuys R. et al., *The Human Central Nervous System*, Springer-Verlag, New York (1981), which references are hereby incorporated by reference.

Typically, in a given test, four consecutive sections from each brain and anatomical level are used, two for the determination of total binding and two for the determination of nonspecific binding. When comparing a pathological with a "control" sample, assays are performed in a matched pair design so that each assay includes sections from at least one pathological brain and its matched control.

Quantitation Of Autoradiograms

Autoradiograms are analyzed by computerized image analysis systems well-known in the art (for example, with the aid of an IBM-PC). The autoradiograms are placed on a light box and a video camera is used for image acquisition. The digitized, reconstructed image is displayed on a monitor and anatomical regions to be measured are traced using a pointing device, such as a mouse, with reference to the histologically stained section. Standard curves derived from the iodine standards are used to convert gray level readings into equivalents of fmol $^{125}$I-iodopindolol / mg tissue. Specific binding is calculated by subtracting nonspecific from total binding.

Statistical Analysis

Standard statistical methods well known in the art, such those present in SAS routines, are used for statistical analysis of the data. Pearson coefficients of correlation are computed to test for age dependence and effects of postmortem delay. Student's t-test (two-tailed), or two- or three-way analyses of variance for unbalanced designs are used to detect the effects of pathological state (e.g. suicide), sex, age and their interactions. It will be readily apparent to one of skill in the art how to modify the statistical methods for analysis of additional variables.

Saturation Binding Studies

Following the characterization and localization of a group effect (such as, for example, age, sex or suicide) by autoradiography, samples from at least one involved region are dissected from the relevant blocks and homogenized for saturation binding studies using well known techniques. For example, the radioligand $^3$H-DHA (dihydroalprenolol) is used as a ligand (see examples below), to generate Kd and Bmax values for total $\beta$AR as well as for the $\beta$1 and $\beta$2 receptor subtypes from Scatchard analysis of the binding data (Scatchard G., *Ann. NY. Acad. Sci.* 51 (1949) 2105–2109).

SPECT Analysis and $^{123}$I-iodopindolol as a SPECT Ligand

Published methods for iodination of pindolol with $^{125}$I (Barovsky, K. et al., supra) are applied to $^{123}$I, an isotope suitable for SPECT. Although the main purpose of the present inventors in developing this imaging agent was to image brain $\beta$AR, it is clear that $^{123}$I-iodopindolol is also useful as both a research and clinical tool for examination of $\beta$AR in other organ systems such as the heart and lungs.

Chemical Synthesis Of $^{123}$I-iodopindolol

In a modification of the method for synthesis of iodopindolol labeled with $^{125}$I (Barovsky et al., supra), $^{123}$I-iodopindolol is prepared. Chloramine-T-induced iodination is initiated with (−) or (+)pindolol enantiomer and quenched with metabisulfite. However, following extraction of the pindolol and its iodinated analogue with ethyl acetate/phenol, the final separation of the radiolabeled product from starting materials may be performed by high performance liquid chromatography (HPLC) using a partisil PAC.M-9 preparative column with 85% dichloromethane and 15% ethanol (containing 1.5% ethylamine and 2.5% water as the eluent (Antoni, G. et al., *Appl. Radiat. Isot.* 40 (1989) 561–564). The solvent is removed by evaporation and the final compound dissolved in an appropriate physiologically buffered solvent. The solution may be sterilized by terminal filtration using a filter such as those available from Millipore. Additionally, other chromatographic systems using previously reported solvent development conditions may be performed for quality assurance.

Based on the theoretical specific activity of 2200 Ci/mmole (for $^{125}$I) and an average human radioactive dose of 5 mCi, the expected human dose of iodopindolol is a trace dose (fractions of a $\mu$g/subject or less than 1 ng/kg body weight)

The acute and subacute toxicity of the cold (decayed) iodopindolol is studied in mice and rabbits. For acute studies, mice and rabbits (10 mice, 6 rabbits/dose) are injected i.v with six doses of iodopindolol, starting with a dose similar to the expected human dose and increasing by 10-fold increments up to 1,000,000 times this dose (e.g., from 1 ng/kg body weight to 1 mg/kg body weight). The animal survival, weight gain and general behavior is monitored over a week. For subacute studies, mice and rabbits are injected daily with 10,000 times the expected human dose (0.01 mg/kg body weight) for 10 days. Body weight is monitored for 2 weeks, at the end of which the animals are sacrificed and organs removed for histopathological examination.

Biodistribution, Metabolism and Radiation Dosimetry

Mice are injected with 10× the expected human dose of commercially available $^{125}$I-iodopindolol. The animals (3 mice/dose, time) are sacrificed at 1 minute, and at 1, 2, 4, 6, 8, and 24 hours after the injection and body organs are removed, weighed and their radioactivity counted in a gamma counter. Brain, thyroid, liver, heart, lung, kidney, adrenals, pancreas, spleen, small and large intestines and ovaries may be examined, as are samples of blood and urine. The % of injected dose present in the organ is calculated from counts of samples of the injectate, and the % of injected dose/gram of tissue is calculated using organ weights. Dosimetry for the $^{123}$I compound can be calculated from Medical Internal Radiation Dosimetry (MIRD) tables (prepared and published by the Society for Nuclear Medicine) using the values obtained from the $^{125}$I isotope, substituting the energy and half life of $^{123}$I.

Trunk blood is collected and centrifuged to yield plasma which is extracted three times with ethyl acetate. The fractions (including the protein pellet) are counted. A portion of the organic fraction is injected onto an HPLC column for separation. Fractions of the HPLC eluent are collected and counted in the gamma counter. The retention time of the HPLC separated products is compared to retention time of the original 125I-iodopindolol to determine if lipophilic metabolites are present.

Testing in Humans

Normal human volunteers are screened to exclude users of medication which might interfere with the labeling of $\beta$AR (e.g., beta blockers) and those allergic to iodine. Magnetic resonance imaging (MRI) scans are obtained using a standard sequence for structural mapping (SE 450/-/30). All subjects undergo routine blood testing, including CBC, an SMA-12 analysis and urinalysis. The blood test may be repeated 3 days after injection of the radiopharmaceutical. Six drops of supersaturated potassium iodide (SSKI) are administered orally 30–60 minutes prior to the injection of the radiopharmaceutical. Subjects are positioned on a gamma camera scanning table. Vital signs and a 2 ml blood sample are obtained. A standard is prepared for later counting. The syringe is counted prior to the injection of 2–5 mCi of $^{123}$I-iodopindolol via a peripheral vein. The syringe is again counted after injection.

Radioimaging

The following describes a preferred imaging protocol: Using a large field of view gamma camera fitted with a general all purpose collimator, a dynamic sample consisting of 1 minute anterior images of the head is obtained up to one hour. At one hour, anterior and posterior whole body images are obtained and may be repeated at 2, 6 and 24 hours post-injection. Whole body counting in comparison with the standard may also be performed at 1 hour and repeated at 2, 6 and 24 hours post injection. Additional 2 ml blood samples are obtained from a peripheral vein (preferably different from the vein used for the administration of the $^{123}$I-iodopindolol) at 1, 5, 15, 30 minutes and at 1, 2, 6 and 24 hours post-injection. Subjects are asked to void their urine prior to the injection of $^{123}$I-iodopindolol, and urine may be collected for the next 24 hours. The blood and urine sample are used for counting and evaluation of metabolites.

At approximately 90 minutes post injection, a single photon emission computed tomography (SPECT) acquisition of the brain is performed. For a general description of SPECT, see: Heller, S. L. et al., *Sem. Nucl. Med.* 17:183–199 (1987); Cerquiera, M. D. et al., *Sem. Nucl. Med.* 17:200–213 (1987); Ell, P. J. et al., *Sem. Nucl. Med.* 17:214–219 (1987)). $^{57}$Co line sources are placed on the subject's head extending bilaterally from the outer canthus to the external auditory meatus. Using a triple-headed gamma camera fitted with high resolution collimators, a total of 120 projections over a 360 degree interval are acquired into a 64×64 matrix. Two simultaneous acquisitions are performed, one using a 20% energy window centered at 159 KeV for the $^{123}$I and one with a 4% energy window centered at 122 KeV for the $^{57}$Co markers. Projection time may be about 60 seconds per projection. With the triple headed camera, this represents about 40 minutes acquisition. This scan time represents a compromise between optimizing counting statistics and patient tolerance, and is preferably shortened for patient studies where possible.

Image Data Processing

Time activity curves are generated for the initial dynamic brain acquisition to determine the rate of uptake in the brain. Analysis of whole body images are performed using regions of interest (ROI's) over appropriate organs (liver, heart, lung, kidney). This provides biodistribution data for comparison with the animal data. Blood clearance curves are generated from the blood data and whole body clearance is calculated from the whole body counts.

Subjects serving as controls for assessment of specific binding receive a single oral dose of the beta blocker propranolol (Inderal, 10 mg) with the SSKI, one hour prior to the brain scan. This permits assessment of the proportion of displaceable ("specific") iodopindolol binding to brain βAR in vivo.

SPECT analysis

SPECT scans are processed and analyzed on the SPARC stations interfaced to the TRIAD gamma cameras ((See also, Heller, S. L. et al., supra, Cerquiera, M. D. et al., supra; Ell, P. J. et al., supra). Reconstruction of both sets of projections with prefiltering and filtered back projection is performed. Attenuation correction is performed using Chang's algorithm. Using gsh, an image display and processing package which runs under UNIX and is implemented on the Sun SPARC stations, the MRI, $^{123}$I-iodopindolol and $^{57}$Co studies are reoriented along the same plane (orbitomeatal) of reconstruction in the transaxial (X-Y) plane, sagittal (Y-Z) plane and coronal (X-Z) plane. Using the markers on the SPECT and the outer canthus and external auditory canal on the MRI, the transaxial levels of the slices are matched and appropriate slice pairs from the $^{123}$I-iodopindolol and MRI data are chosen. Using a polynomial warping algorithm (Maguire G. Q. et al., *Information Processing in Medical Imaging*, Bacharach, S, L,, ed., Martinus Nijhof, Dordrecht (1986), pp. 266–279, which reference is hereby incorporated by reference), implemented under qsh, regions of interest which are generated on the MRI are interpolated onto the SPECT slice. Matching of phantom studies has shown that MRI and SPECT regions can be matched within 1–2 pixels of each other.

Semiquantitative analysis is performed using average count density in the region of interest compared to the average count density of the whole brain. The rank order of the ratios can be compared to the rank order of βAR density in the same brain regions derived from autoradiography.

Patient Analysis

Depressed, suicidal patients are screened by psychiatric personnel skilled in the art of diagnosis of affective disorders. Suicidal patients are classified as those who meet DSMIII-R (*Diagnostic and Statistical Manual of Mental Disorders*, American Psychiatric Association Committee on Nomenclature and Statistics, 3rd ed., American Psychiatric Association, Washington DC, 1980) criteria for major depression and have recently attempted suicide, thus creating the best match for the group of subjects studied postmortem. Both the Hamilton depression rating scale (HDRS) (Hamilton, J., *J. Neurol. Neurosuro. Psychiat.* 23:56–62 (1960)) and the Beck depression inventory (BDI) (Beck, A. T. et al., *Arch. Gen. Psychiat.* 4:53–63 (1961) are administered. All patients are preferably drug free for at least two weeks before the initial scan. Control subjects are recruited from the community and administered the HDRS and BDI. Patients and controls may also be screened for the absence of drug abuse, alcoholism, neurological disorders and psychiatric disorders other than depression.

Patients undergo an MRI brain scan using a standard sequence for structural mapping (SE 450/-/30). Individual MRI scans, rather than standard atlas definitions of ROI's are essential since there is evidence for structural differences between the brains of depressed patients and controls revealed by MRI (Coffey, C. E. et al., *J. Neuropsychiat.* 1 (1989) 135–144). SPECT acquisition and analysis is performed as described above.

Where group difference are present (e.g patients have higher βAR levels in prefrontal cortex than controls), the patients are started on a therapeutic regimen (antidepressant or ECT) according to the judgment of their attending physician. Approximately 3 months later, the controls are re-scanned to assess test-retest reproducibility over time and the patients are scanned again following clinical evaluation. Regional changes in βAR are subjected to correlation with changes in clinical state. Statistical analysis is performed as described above.

The present invention also provides kits which are useful for diagnosing an alteration or normalization of beta adrenergic receptors in a tissue, preferably brain, in a subject using a radioimaging technique such as those described above; this kit contains a set of one or more standard control radiographic images of the tissue having normal density and distribution of the receptors, wherein the information obtained by the radioimaging technique can be compared to the radiographic images contained in the kit to allow determination of the alteration or normalization of receptor expression. The normal images may be derived from autoradiograms (see above) from post-mortem brains. The normal data may be expressed as two-dimensional images, such as photographs of an autoradiogram, or as three dimensional images in the form of digitized computer data (see above).

In order to utilize such a kit, a physician, for example, compares the stored two- or three-dimensional images of the tissue, e.g., brain, being analyzed with a two- or three-dimensional standard control autoradiogram. By selecting the appropriate anatomic sites readily apparent to one of skill in the art, a determination can be made whether a particular brain region, viewed as a section, for example, has normal or abnormal levels of beta adrenergic receptors.

In a preferred embodiment, the autoradiographic images in the kit are those taken from brains of suicidally depressed individuals, which show enhanced numbers of beta adrenergic receptors as described herein. Comparison with such "standards" and/or with normal brain "standards," will assist in the diagnosis of suicidal depression.

Having now generally described the invention, the same will be more readily understood through reference to the following examples which are provided by way of illustration, and are not intended to be limiting of the present invention, unless specified.

EXAMPLE I

REGIONALLY SELECTIVE INCREASES IN β-ADRENERGIC RECEPTOR DENSITY IN THE BRAINS OF SUICIDE VICTIMS

Fourteen suicide and 14 pair-matched control brains were collected over 3 years from the medical examiner's offices in New York City and Jaffa, ISRAEL. The interval between death and autopsy (PMD, postmortem delay) was below 48 hours, a period in which most membrane receptors have been shown to be quite stable (Hardy et al., *Neurochem. Int.* 5:253–266 (1983)). The results of the coroner's examination as well as the results of broad-spectrum toxicological tests performed by the forensic laboratory were made available within 8 weeks. Only drug-free and pathology-free brains were included. For each suicide brain, a control matched for sex and age group with a PMD under 48 hours was collected the same day or within a few days, so that the pairs are also matched for storage time. The brains from each pair were dissected or sectioned on the same day and receptors were labeled in the same experiment, by an experimenter blind to the identity of the samples.

The brains were removed at autopsy and the right hemisphere sliced in the coronal plane. The slices, about 2 cm thick, were examined for signs of pathology and frozen in powdered dry ice, then removed for long-term storage at −80° C. Grey matter from the most frontal slice (prefrontal cortex) was dissected with a scalpel and homogenized. Crude membrane preparations were made from the homogenates, divided and stored frozen for saturation binding assays. The other slices were used for autoradiography. Eight concentrations of [$^3$H]DHA (New England Nuclear, specific activity: 72 Ci/mmol), ranging from 0.1 to 4 nM were incubated with samples of the membrane preparations, with parallel incubates containing $10^{-6}$M propranolol to establish non-specific binding (Biegon et al., *Life Sci.* 32:2015-2022 ;(1983)); Enna et al., *J. Neurochem.* 28:233-236 (1983)). β-Receptor subtypes were distinguished by coincubation of the radioligand $10^{-6}$ M concentrations of either zinterol, a $β_1$-selective blocker, or meterolol, a $β_2$-selective blocker, in 5 out of the 10 pairs included in this part of the study (Ecker et al., *Int. Catecholamine Symp. Abstr.* 6:52 (1987)). The affinity ($K_d$ and maximal density ($B_{max}$) of the receptors were derived from Scatchard analysis (Scatchard G., *Ann. N.Y. Acad. Sci.* 51:660-672 (1949)) of the binding data and protein was assayed by the method of Lowry et al.(Lowry et al., *J. Biol. Chem.* 193:265-275 (1951)).

For autoradiography, slices from frontal cortical and anterior basal ganglia levels were sectioned in a Bright Cryotome (a refrigerated whole-body microtome) at −15° C. Sections of 40 μm were thaw- mounted onto gelatin-coated glass slides and βARs were labeled with [$^{125}$I]iodopindolol (Pazos et al., *Brain Res.* 358:324-328 (1982)); Rainbow et al., *Proc. Natl. Acad. Sci. U.S.A.*, 81:1585-1589 (1984)). Receptors were labeled with 150 pM iodopindolol, with or without $10^{-6}$ M propranolol to define non-specific binding. The autoradiograms were developed after 48 or 72 hours. Values of optical density were converted to fm of receptor per mg tissue via brain mash standards containing known amounts of radioactive iodine (Rainbow et al., *Proc. Natl. Acad. Sci. U.S.A.*, 81:1585-1589 (1984)). Non-specific binding was subtracted from all readings. Quantitative analysis of the autoradiograms was accomplished using a computerized image analysis system based on an IBM PC-AT, a frame grabber board from Imaging Technology and customized software.

Figure 1:
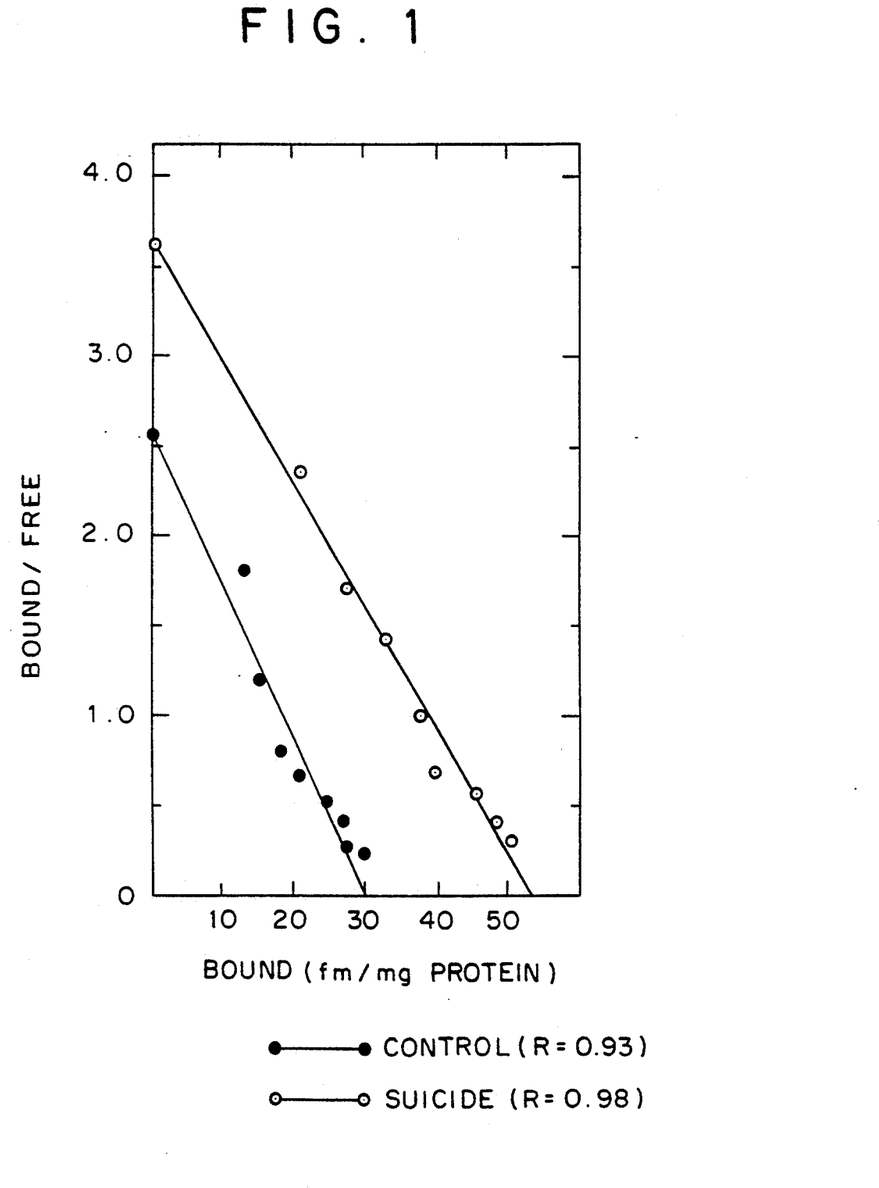
FIG. 1 shows representative Scatchard plots of $\beta$-adrenergic receptor binding in frontal cortical homogenates from a suicide and a control subject. The regression line was determined by computerized least square analysis. R=correlation coefficient.

The binding characteristics of βARs were studied in prefrontal cortical homogenates from 10 pairs. The region corresponds to Brodmann's areas 9 and 10. The receptor density was significantly increased in the suicide group as compared to the control. Increases in binding ranging from 30% to 115% (mean: 48%) were observed in 9 of the 10 pairs included in this part of the study (P<0.0003, Student's t-test for paired values, Table 1). There was no significant change in receptor affinity ($K_d$) in the same subjects, although a trend towards lower affinity (increased $K_d$ values) was apparent (Table 1, FIG. 1). An analysis of variance by age (old vs. young), sex and suicide revealed no significant effects of age or sex, the

TABLE I

β-ADRENERGIC RECEPTOR BINDING PARAMETERS IN PREFRONTAL CORTICAL HOMOGENATES FROM SUICIDES AND CONTROLS

| Pair no. | Sex | | Age (yrs) | | PMD (h) | | Bmax (fm/mg P) | | Kd (nM) | |
|---|---|---|---|---|---|---|---|---|---|---|
| | C | S | C | S | C | S | C | S | C | S |
| 1 | F | F | 17 | 28 | 24 | 18 | 65 | 108 | 0.84 | 0.98 |
| 2 | F | F | 17 | 21 | 25 | 21 | 92 | 81 | 0.8 | 0.9 |
| 3 | M | M | 30 | 22 | 8 | 5 | 44 | 85 | 0.3 | 1.5 |
| 4 | M | M | 49 | 45 | 31 | 18 | 31 | 67 | 0.3 | 0.9 |
| 5 | M | M | 57 | 54 | 8 | 16 | 86 | 119 | 0.4 | 1.2 |
| 6 | M | M | 61 | 74 | 48 | 24 | 55 | 97 | 0.6 | 1.4 |
| 7 | M | M | 25 | 28 | 18 | 22 | 78 | 106 | 0.6 | 1.1 |
| 8 | M | M | 65 | 65 | 13 | 18 | 36 | 58 | 1.25 | 1.0 |
| 9 | M | M | 69 | 62 | 6 | 35 | 32 | 53 | 0.4 | 0.4 |
| 10 | M | M | 29 | 43 | 30 | 24 | 53 | 83 | 1.5 | 0.8 |
| Mean ± | | | 43.0 | 44.3 | 20.0 | 19.7 | 57.7 | 86.0 | 0.6 | 1.0 |
| SEM | | | 7 | 7 | 4.5 | 2.6 | 7.9 | 7.8 | 0.1 | 0.1 |

P < 0.0003. Student's t-test for paired value
C. control; S. suicide; M, male; F, female; Bmax is expressed in femtomoles per mg protein; Kd is expressed in nanomolar; PMD: post-mortem delay (in hours).

only significant main effect was that of suicide. There was no significant correlation between age or postmortem delay and receptor binding.

When $β_1$- and $β_2$-adrenergic receptors were measured separately in 5 of the 10 pairs, a significant increase in the $B_{max}$ (but no change in $K_d$) was found in β1-receptors ($B_{max}$, control: 37.7±9.3 fm/mg protein, suicide: 50.3±9.4 fm/mg protein, P<0.015, paired t-test; $K_d$, control: 2.2±0.5 nM vs. suicide:1.7±0.3 nM, n=5).

The $β_2$-receptors showed a trend towards an increased $B_{max}$ which did not reach statistical significance ($B_{max}$, control: 28.0±4.0 fm/mg protein, suicide: 39.2±3.1 fm/mg protein; p=0.1, paired t-test; $K_d$, control: 1.1±0.13 vs. suicide: 1,3±0.27 nM).

Tissue sections from 4 pairs included in the homogenate study and 5 additional pairs were analyzed by autoradiography (Table II). Significantly increased βAR binding was observed in some frontal cortical regions; the cingulate and superior frontal gyrus, but not in the inferior frontal gyrus, caudate, putamen or cortical white matter The increase was observed in all cortical layers.

TABLE II

β-ADRENERGIC RECEPTOR BINDING MEASURED BY QUANTITATIVE AUTORADIOGRAPHY OF BRAIN SECTIONS FROM SUICIDES AND CONTROLS

| Brain Region | n | [125I]iodopindolol bound fm/mg tissue | |
|---|---|---|---|
| | | Control | Suicide |
| Cortical gyri | | | |
| cingulate | 8 | 11.8 ± 3.3 | 16.0 ± 2.7* |
| frontalis superior | 9 | 10.8 ± 2.6 | 17.2 ± 2.9** |
| frontalis medius | 8 | 9.3 ± 4.0 | 16.7 ± 3.5 |
| frontalis inferior | 6 | 14.2 ± 4.0 | 17.2 ± 4.1 |
| Basal ganglia | | | |
| caudate | 5 | 13.2 ± 4.0 | 15.4 ± 2.0 |
| putamen | 5 | 19.5 ± 1.1 | 17.4 ± 2.5 |
| white matter (cortical) | 9 | 5.6 ± 1.8 | 6.7 ± 0.7 |

*P < 0.04, **P < 0.03, Student's t-test for paired values performed on n pairs. Results are mean ± S.E.M. of 2-6 readings/region from each of n subjects. The pairs were matched for sex (2 females, 7 males/group) Age (controls: 50.2 ± 6.4; suicides 46.9 ± 6.4 years) and postmortem delay (controls: 20.5 ± 3; suicides: 19 ± 1 h). The causes of death in this sample, in decreasing order of frequency, was: multiple trauma, gunshots, suffocation and drowning. There was no cases of death following a prolonged period of anoxia.

The results indicate that βAR density is increased in the brains of suicide victims. Moreover, this increase in receptor number is expressed in select brain readings.

This is the first study in which receptor autoradiography was used to compare the brains of suicides and controls and to show such anatomically localized changes. The ability to demonstrate these changes was due to the rigorous matching of the suicide and control groups and the exclusion from the study of brains containing tricyclic antidepressants or any other centrally acting drugs. Such control measures were not utilized in previously published reports of no change in a β-receptors following suicide (Crow et al., *Neuropharmacology* 23:1561-1569 (1984)); Meyerson et al., *Pharmacol. Biochem. Behav.* 17:159-163 (1982)). A better controlled study showed an increase in single-point DHA binding in homogenates of prefrontal cortex from suicide victims (Mann et al., *Arch. Gen. Psychiat.* 43:954-959 (1986)).

The present results also support the notion that one subtype of the βAR ($\beta_1$) (Minneman et al., *Science.* 204:866-868 (1979)) is more sensitive to the pathological state associated with suicide than the other subtype. The selectivity of the phenomenon is further enhanced by the observation of no change in cholinergic muscarinic receptors of the $M_1$-subtype in the same subjects ($B_{max}$ control, 290±18; suicide, 317±22.5 fm/mg protein; means ±S.E.M., n=10)

The cause of the increased βAR binding in the suicide brains is not known. It may reflect a postsynaptic adaptive response to decreased presynaptic activation, a phenomenon well documented for this receptor type in experimental animals (Sporn et al., *Mol. Pharmacol.,* 13:1170-1180 (1977)). Alternatively or in addition, these changes may indicate deregulation of genomic and nongenomic factors regulating density. Disturbances in the serotonergic system (Lloyd et al., *Adv. Biochem. Psychopharmacol.,* 11:387-398 (1974)); Shaw et al., *Br. J. Psychiatry.* 113:1407-1411 (1975); Stanley et al., *Science,* 216:1337-1339 (1982)) could also lead to abnormalities in βAR function, since a functional linkage between the two systems has been recently demonstrated (Janowsky et al., *Science,* 218:900-901 (1982)). It is important to note that the effects of tricyclic antidepressants and electroconvulsive shock on βAR density are anatomically selective, being evident in some cortical and hippocampal regions but not in the striatum, based on both autoradiographic and homogenate binding techniques (Bergstrom et al., supra; Biegon A., *J. Neurochem,* 47:77-80 (1986)), Biegon et al., *Eur. J. Pharmacol.* 123:329-334 (1986)), Stanford et al., *Neuroscience,* 7:1753-1757 (1982)).

EXAMPLE 11

CHARACTERIZATION AND LOCALIZATION OF βAR IN POSTMORTEM BRAINS: EFFECTS OF SEX, AGE AND SUICIDE

The results presented in this example are based on 26 brains and 3 coronal levels. Significant and regionally selective effects of sex, age and suicide have been found in this population using quantitative autoradiography of $^{125}$I-iodopindolol. The sex effects are large enough to influence the overall cortical distribution pattern of the receptors, so that it has to be described separately for males and females.

In males, there is a pronounced cortical gradient in receptor density, going from low prefrontal levels to high occipital cortical binding. Within the cortical gyri, binding is usually more dense over the external cortical layers (FIG. 1). women have considerably higher densities of βAR in the prefrontal cortex (Table III), resulting in a parabolic rather than linear fronto-occipital cortical distribution. The same pattern (increased binding in prefrontal cortex only) is observed in the suicide victims in comparison to controls. These results predict a difference in the pattern of receptor distribution, rather than small quantitative changes, in women and suicidal patients. Since women are 2-3 times more likely than men to from depression, the fact that women have higher βAR levels than men in prefrontal cortex also supports the relevance of these receptors and this particular brain region to depression.

The distribution of βAR in the subcortical regions studied so far is similar in men and women, suicides and controls, with the highest levels found in the hippocampus, with dentate gyrus >CA fields >subiculum. Moderately high levels are found in the head and tail of the caudate which is higher than putamen, followed by detectable, but relatively low, levels in globus pallidus. Within the globus pallidus, the lateral division has more binding than the medial. Thalamic nuclei were heterogeneously labeled, with moderately high levels in the medial and low levels in the ventrolateral nuclei (Table IV).

TABLE III

Effect of sex and suicide on [$^{125}$I]iodopindolol binding in prefrontal cortex.

| | MALE | | FEMALE | | |
| region: | n | mean ± s.e.m. | n | mean ± s.e.m. | ANOVA |
| --- | --- | --- | --- | --- | --- |
| superior frontal gyrus | | | | | |
| external band | 16 | 0.87 ± 0.09 | 6 | 1.48 ± 0.25 | + |
| internal band | 16 | 0.82 ± 0.07 | 6 | 1.24 ± 0.12 | + |
| medial frontal gyrus | | | | | |
| external band | 13 | 0.77 ± 0.12 | 5 | 1.36 ± 0.23 | +, # |
| internal band | 12 | 0.71 ± 0.10 | 5 | 1.09 ± 0.16 | |
| inferior frontal gyrus | | | | | |
| external band | 11 | 0.86 ± 0.13 | 5 | 1.08 ± 0.19 | # |
| internal band | 11 | 0.78 ± 0.13 | 5 | 0.99 ± 0.16 | |
| orbital gyri | | | | | |
| external band | 11 | 0.77 ± 0.12 | 4 | 1.46 ± 0.25 | + |
| internal band | 10 | 0.70 ± 0.10 | 4 | 1.24 ± 0.18 | + |
| gyrus rectus | | | | | |
| external band | 9 | 0.93 ± 0.18 | 3 | 1.42 ± 0.13 | |
| internal band | 9 | 0.80 ± 0.13 | 3 | 1.24 ± 0.23 | +, # |
| cingulate gyrus | | | | | |
| external band | 10 | 0.99 ± 0.18 | 4 | 1.20 ± 0.31 | * |
| internal band | 10 | 0.87 ± 0.16 | 4 | 1.31 ± 0.24 | |
| WHITE MATTER | 16 | 0.46 ± 0.04 | 6 | 0.78 ± 0.09 | |

Results represent mean ± s.e.m. specific binding in n brains, expressed as fmol [$^{125}$I]iodopindolol/mg tissue.
ANOVA column presents results of a two way (suicide*sex) analysis of variance corrected for unbalanced designs, where:
* - significant (p<0.05) suicide effect
+ - significant (p<0.05) sex effect
- significant (p<0.05) interaction

TABLE IV

| | Age dependence of BAR distribution in the human brain | | | | | | |
| | MALE | | | FEMALE | | | |
| REGION: | N | Mean ± s.e.m. | R(p) | N | Mean ± s.e.m. | R(p) | ANOVA |
| --- | --- | --- | --- | --- | --- | --- | --- |
| superior temporal gyrus | | | | | | | |

TABLE IV-continued

Age dependence of βAR distribution in the human brain

| REGION: | MALE | | | FEMALE | | | ANOVA |
|---|---|---|---|---|---|---|---|
| | N | Mean ± s.e.m. | R(p) | N | Mean ± s.e.m. | R(p) | |
| external band | 14 | 1.13 ± 0.16 | | 6 | 1.18 ± 0.18 | | |
| internal band | 14 | 1.18 ± 0.15 | −0.64(0.01) | 6 | 1.04 ± 0.13 | | |
| medial temporal gyrus | | | | | | | |
| external band | 13 | 1.05 ± 0.18 | | 6 | 1.03 ± 0.15 | | |
| internal band | 13 | 1.18 ± 0.17 | −0.63(0.02) | 6 | 1.06 ± 0.15 | | * |
| inferior temporal gyrus | | | | | | | |
| external band | 13 | 1.04 ± 0.16 | −0.66(0.01) | 5 | 1.21 ± 0.14 | | |
| internal band | 13 | 1.14 ± 0.17 | | 6 | 1.11 ± 0.17 | | |
| lateral occipitotemporal gyrus | | | | | | | |
| external band | 13 | 0.94 ± 0.13 | −0.66(0.01) | 6 | 0.93 ± 0.19 | | |
| internal band | 13 | 1.02 ± 0.14 | −0.79(0.001) | 6 | 0.86 ± 0.11 | | |
| parahippocampal gyrus | | | | | | | |
| external band | 13 | 1.07 ± 0.19 | −0.75(0.003) | 7 | 1.22 ± 0.32 | | |
| internal band | 13 | 0.95 ± 0.15 | −0.80(0.001) | 6 | 1.01 ± 0.23 | | * |
| entorhinal cortex | 10 | 1.00 ± 0.19 | | 3 | 0.94 ± 0.33 | | |
| BASAL GANGLIA | | | | | | | |
| caudate nucleus | | | | | | | |
| head | 5 | 1.45 ± 0.34 | | | | | |
| tail | 14 | 1.39 ± 0.23 | −0.70(0.005) | 8 | 1.15 ± 0.17 | | |
| putamen | 11 | 1.24 ± 0.18 | −0.66(0.02) | 6 | 1.05 ± 0.22 | | * |
| claustrum | 9 | 0.86 ± 0.14 | −0.72(0.02) | 5 | 0.64 ± 0.18 | | |
| globus pallidus | | | | | | | |
| medial | 8 | 0.73 ± 0.17 | −0.72(0.05) | 3 | 0.44 ± 0.09 | | |
| lateral | 8 | 0.85 ± 0.20 | −0.80(0.02) | 5 | 0.78 ± 0.16 | | * |
| HIPPOCAMPUS | | | | | | | |
| CA fields | | | | | | | |
| pyramidal layer | 13 | 1.74 ± 0.26 | | 4 | 1.70 ± 0.26 | | |
| molecular layer | 13 | 1.74 ± 0.26 | | 4 | 1.70 ± 0.40 | | |
| dentate gyrus | 10 | 1.94 ± 0.45 | | 5 | 1.88 ± 0.32 | | |
| subiculum | 12 | 1.36 ± 0.20 | | 5 | 1.35 ± 0.33 | 0.91(0.03) | |
| WHITE MATTER | 18 | 0.59 ± 0.07 | | 8 | 0.47 ± 0.09 | | |

Table presents mean ± s.e.m. fmol [$^{125}$I]iodopindolol/mg tissue specifically bound, in N brains.
ANOVA column presents significant interaction in a two way (sex*age) analysis of variance for unbalanced designs.
* - p<0.05.
R - Spearman coefficient of correlation between specific binding of iodopindolol and age.

βAR exhibit a strong age-dependence in some but not all of the brain regions analyzed. Significant age related decreases in βAR binding are found in men only. Negative correlations between βAR binding and age were detected in parietal frontal but not prefrontal cortical gyri, and were especially pronounced in the temporal cortex, with correlation coefficients ranging from −0.64 to −0.9 (significance levels of 0.04 to 0.001, Table III). Significant declines in βAR binding were found also throughout the basal ganglia (r= −0.66–0.8, 0.005<p<0.05) but not in hippocampus. This sex- and region-specific pattern of age effects is similar to what has been observed in other neurotransmitter systems, e.g. dopamine receptors studied by PET in vivo (Wong D. F. et al. Science 226:1393–96 (1984)) and serotonergic uptake sites and postsynaptic receptors measured by quantitative autoradiography postmortem (Gross-Isserof, R. et al. 1988, 1990, supra).

Figure 2:
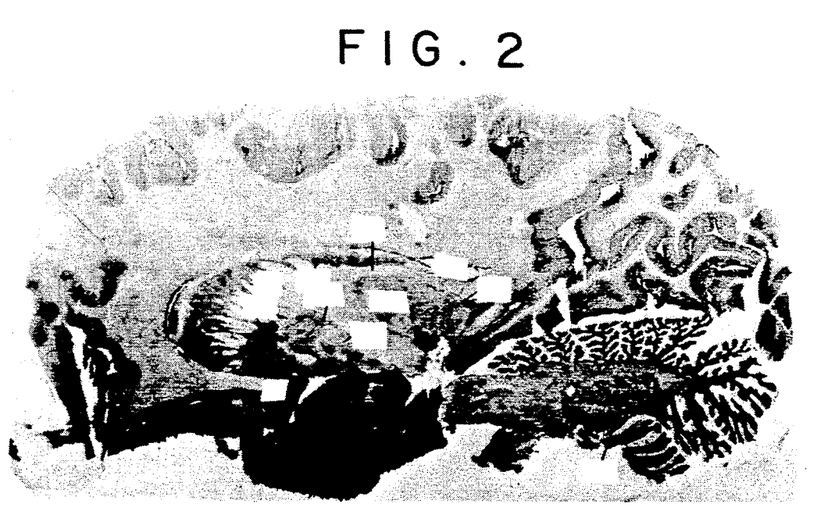
FIGS. 2-4 shows autoradiograms depicting the distribution of $\beta$-adrenergic receptors in the human brain. F=prefrontal cortex, C=caudate, H=hippocampus, T=thalamus (pulvinar), O=occipital cortex)
Figure 3:
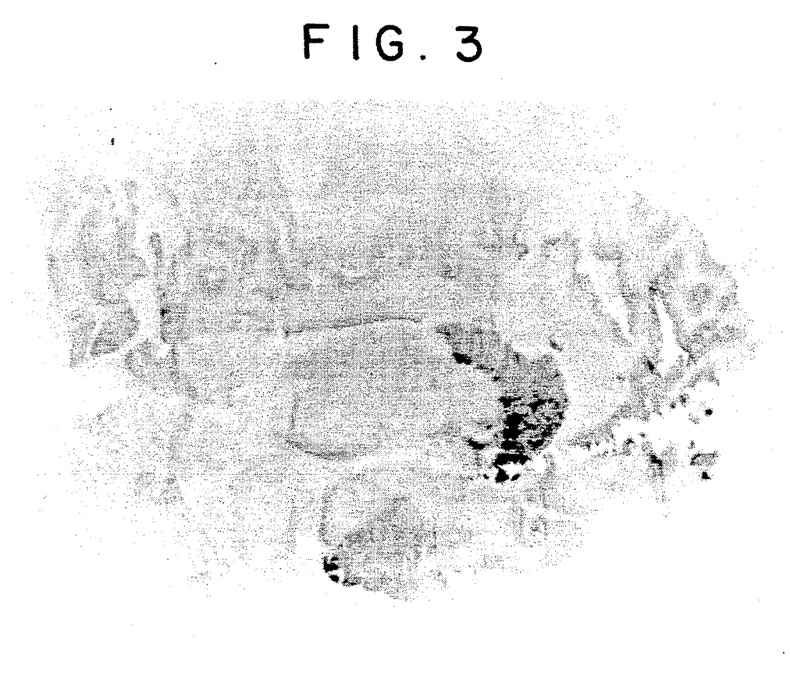
Figure 4:
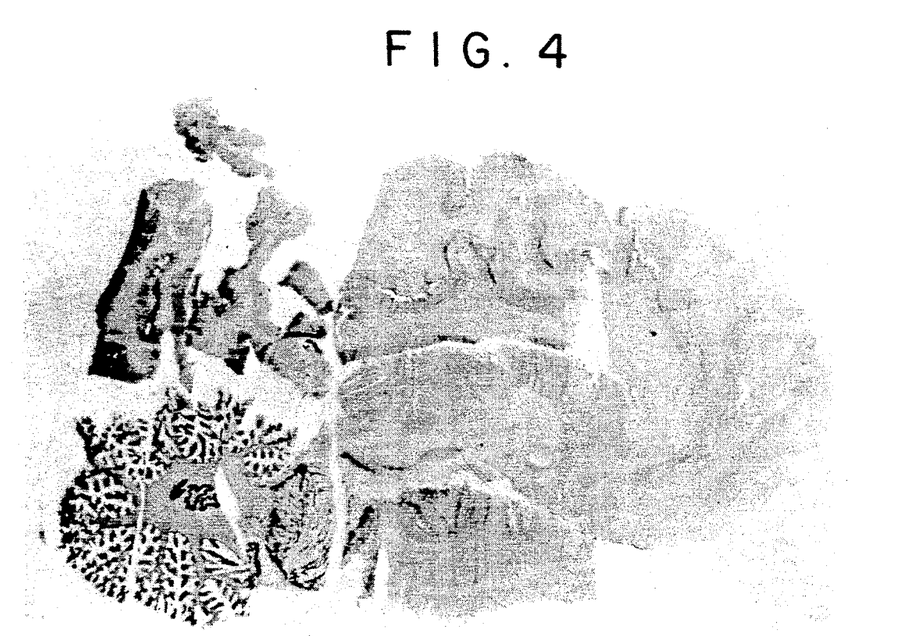

To evaluate possible subtype specificity of these effects, β1 and β2 receptor subtypes were mapped (FIGS. 2–4). β1 receptors predominate in the prefrontal cortical external layers and in basal ganglia (FIG. 3). β2 receptors are found in internal cortical layers and predominate in hippocampus, cerebellum and white matter (FIG. 4). The prevalence of β1 receptors in prefrontal cortex has been confirmed by saturation binding assays on homogenates of frontal superior gyrus using $^3$H-DHA (dihydroalprenolol) as a ligand, with 0.1 μM zinterol or metoprolol included in the incubation buffer for subtype differentiation (see below). Based on 3 brains, a total Bmax of 50–100 fm/mg protein was calculated, with the β1 receptor subtype accounting for the majority of the sites (Bmax: 40–60 fm/mg protein) and a smaller β2 receptor fraction (Bmax: 25–40 fm/mg protein). The Bmax values for the two subtypes added up to total specific binding in each individual brain, confirming the use of the two blocker concentrations for receptor subtype differentiation.

EXAMPLE III

EVALUATION AND DEVELOPMENT OF IODOPINDOLOL AS A LIGAND FOR SPECT IMAGING OF βAR IN VIVO

Brain distribution, whole body distribution and radiation dosimetry of iodopindolol is studied using the commercially available $^{125}$I-iodopindolol. In parallel, the synthesis of $^{123}$I-iodopindolol is performed using the procedure for $^{125}$I described in the literature (Barovsky et al., supra).

In vivo autoradiography was been used to study brain distribution and kinetics of iodopindolol. Groups of rats (3 per treatment/time) were injected intravenously (i.v.) in the tail vein with 250 μCi/kg $^{125}$I-iodopindolol, either alone or 5 min after an intraperitoneal injection of the βAR antagonist (beta blocker) propranolol (5 mg/kg), to define nonspecific binding. Animals were sacrificed by decapitation 15, 30, 60 and 90 minutes post- injection and the brains quickly removed. The right hemisphere and a blood sample were used for direct counting while the left hemisphere was frozen immediately on dry ice and then sectioned sagittally. Sections were apposed to hyperfilm for one week.

Figure 5:
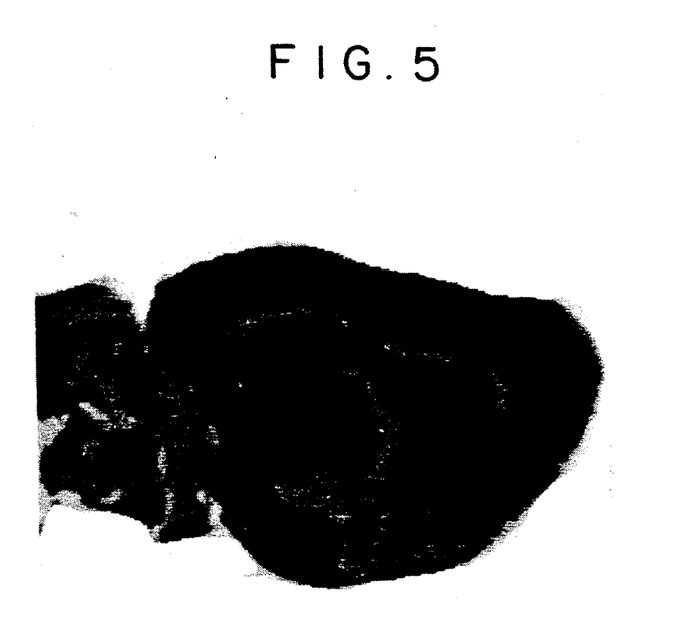
FIG. 5 is an autoradiogram showing the brain distribution of iodopindolol injected in vivo in the rat (sagittal section) from an animal sacrificed 15 minutes post injection of iodopindolol. fc=frontal cortex, cd=caudate, cb=cerebellum. At this time point, there is no apparent difference between animals injected with iodopindolol alone and those pretreated with propranolol.

At 15 and 30 minutes post-injection there was a very small difference between "total" and "nonspecific"

binding to brains, and all gray matter areas on the autoradiograms looked almost uniformly dark (FIG. 5). By 60 and 90 minutes, animals pre-injected with propranolol showed low and uniform brain binding of radiolabel (FIG. 7), while the animals given iodopindolol without propranolol exhibited a distribution of binding in the brain which was identical to the binding observed following in vitro incubation with the radioligand: high levels in frontal cortex, caudate, and cerebellum; moderate to low levels in various hippocampal structures and thalamic nuclei; low levels in brain stem and medulla (FIG. 6, Rainbow, T. C. et al., *Proc. Natl. Acad. Sci. USA* 81 (1984) 1585-1589).

Figure 6:
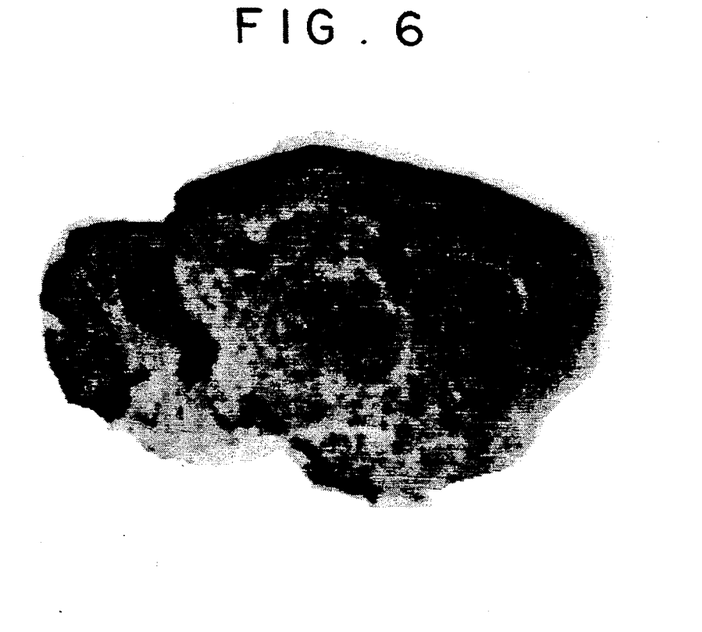
FIG. 6 is an autoradiogram at the same anatomical level as FIG. 5, from an animal sacrificed 60 minutes post injection. The distribution of radioactivity, showing relatively high levels in external cortical layers, caudate and cerebellum and relatively low levels in hippocampus, matches the distribution of rat brain $\beta$-adrenergic receptors measured in vitro.
Figure 7:
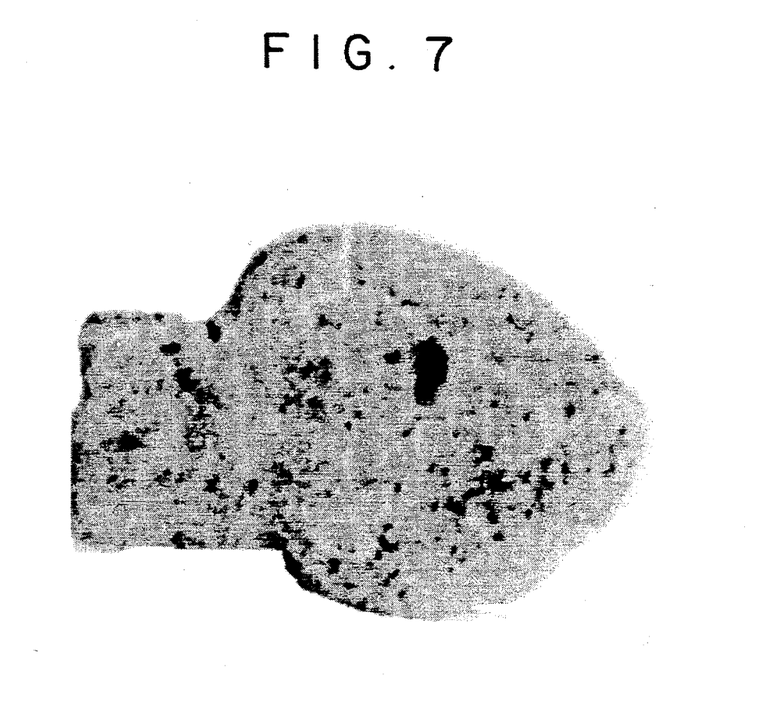
FIG. 7 is an autoradiogram showing the brain distribution of iodopindolol injected in vivo in the rat (sagittal section) from an animal pretreated with propranolol and sacrificed 60 minutes after the injection of iodopindolol.

The only apparent exceptions were regions on the blood side of the blood brain barrier, such as the choroid plexus (responsible for the high density apparent in the ventricular regions in FIGS. 5-7) and the pineal gland, which are relatively darker on the in vivo autoradiogram. These results demonstrate that one hour after injection, most of the present in the brain specifically labels $\beta$AR. The brain levels of bound radiolabel do not decline appreciably between 60 and 90 minutes. This time course is particularly suitable for imaging with isotopes having a moderately long half life such as the preferred radioligand of the present invention, $^{123}$I (13.5 hours).

Whole body distribution studies were performed in female BALB/c mice injected via the tail vein with 500 μCi/kg $^{125}$I-iodopindolol Animals were sacrificed by cervical dislocation 1 min or 120 min post-injection, At 1 minute post-injection, the highest concentrations of radioactivity (counts/gram of tissue) were found in the lungs, followed by heart and other organs. Urine levels were below the threshold of detection at this time point. Brain levels were about 1/5 of blood levels (mCi per gram of brain / mCi per ml blood) and accounted for less then 1% of injected dose. Two hours later, the highest activity was found in urine, followed by lung, heart and brain. Brain levels were 0.06% of total injected dose at this time point, corresponding to less than 1% receptor occupancy (based on a Bmax of approximately 2 pmole/gram brain, extrapolated from rat and human values).

In a subsequent study, whole body distribution was examined in mice following tail vein injection of 2 μCi $^{125}$I-iodopindolol. Animals were sacrificed at various time points up to 22 hours post-injection. Percent injected dose (%ID) was determined in 11 organs, blood and urine. At one minute, lungs contained the highest %ID (17%), heart 3-4 %ID and brain 0.3%ID. Brain levels remained stable until two hours post-injection. Lung radioactivity declined; stomach and intestine radioactivity increased. Between 2-4 hours post-injection, radioactivity fell in all organs.

While these results indicate that brain uptake of iodopindolol is hindered by the blood brain barrier, the percentage found in the brain is still sufficient for detection by the more sensitive, higher resolution SPECT cameras. Since iodopindolol, like all beta blockers, binds to $\beta$AR on lymphocytes and other leucocytes, retention in blood is expected. However, since the blood volume represents only a small fraction of total brain volume, this is not an undue complication.

The references cited above are all incorporated by reference herein, whether specifically incorporated or not.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims. It is to be understood that the phraseology or terminology herein is for the purpose of description and not of limitation.

What is claimed is:

1. A method for radioimaging beta adrenergic receptors in brain tissue of a live animal comprising:
   (a) administering intravenously an in vivo beta adrenergic imaging agent comprising an $^{124}$I or $^{123}$I radioisotope of iodopindolol and an administering medium;
   (b) allowing a sufficient amount of time for both (i) said imaging agent to enter the brain tissue to be imaged and (ii) a detectable portion of said compound to become selectively bound to said adrenergic receptors in said brain tissue; and
   (c) recording a radioimage of said adrenergic receptor containing brain tissue using a radioimaging technique selected from positron emission tomography when said I$^{123}$ or I$^{124}$ is used or single photon emission computed tomography when said I$^{123}$ is used.

2. A method according to claim 1 wherein said animal is a human.

3. A method according to claim 1 wherein said radioisotope is $^{123}$I and said radioimaging technique is single photo emission computed tomography (SPECT).

4. A method according to claim 1 wherein said radioisotope is $^{124}$I and said radioimaging technique is positron emission tomography (PET).

* * * * *